(12) United States Patent
Sakaguchi

(10) Patent No.: US 9,408,760 B2
(45) Date of Patent: Aug. 9, 2016

(54) DISPOSABLE DIAPER

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 5 days.

(21) Appl. No.: 14/389,226

(22) PCT Filed: Mar. 28, 2013

(86) PCT No.: PCT/JP2013/059261
§ 371 (c)(1),
(2) Date: Sep. 29, 2014

(87) PCT Pub. No.: WO2013/147023
PCT Pub. Date: Oct. 3, 2013

(65) Prior Publication Data
US 2015/0051570 A1    Feb. 19, 2015

(30) Foreign Application Priority Data

Mar. 30, 2012  (JP) ................................. 2012-081159

(51) Int. Cl.
*A61F 13/15* (2006.01)
*A61F 13/49* (2006.01)
*A61F 13/536* (2006.01)
(Continued)

(52) U.S. Cl.
CPC ..... *A61F 13/49017* (2013.01); *A61F 13/15203* (2013.01); *A61F 13/533* (2013.01); *A61F 13/536* (2013.01); *A61F 13/5323* (2013.01); *A61F 2013/15357* (2013.01)

(58) Field of Classification Search
CPC ................ A61F 13/533; A61F 13/536; A61F 13/15357; A61F 13/49001; A61F 13/49039; A61F 13/49041; A61F 13/5312; A61F 13/53436
See application file for complete search history.

(56) References Cited

U.S. PATENT DOCUMENTS 4,685,915 A * 8/1987 Hasse ................... A61F 13/532
                                                             604/378
6,702,800 B1    3/2004 Vukos et al.
(Continued)

FOREIGN PATENT DOCUMENTS

EP      1459718 A1    9/2004
JP   2002-209942 A    7/2002
(Continued)

OTHER PUBLICATIONS

Office Action dated Jun. 18, 2015, corresponding to Chinese patent application No. 201380016619.5.
(Continued)

*Primary Examiner* — Bradley Philips
(74) *Attorney, Agent, or Firm* — Hauptman Ham, LLP

(57) ABSTRACT

An absorber of a disposable diaper includes a first region at least partially arranged in the crotch stretch unit and a second region arranged adjacent to the first region at an outer side from the first region in the product longitudinal direction and having a lower bending rigidity than that of the first region. A boundary between the first region and the second region is arranged at an outer side from an outer end of the crotch stretch unit in the product longitudinal direction and is arranged at an inner side from an outer end of the leg stretch unit in the product longitudinal direction.

14 Claims, 5 Drawing Sheets

(51) Int. Cl.
*A61F 13/532* (2006.01)
*A61F 13/533* (2006.01)

(56) References Cited

U.S. PATENT DOCUMENTS

| | | |
|---|---|---|
| 7,381,203 B2 | 6/2008 | Kasai |
| 7,642,398 B2 | 1/2010 | Jarpenberg et al. |
| 7,972,319 B2 | 7/2011 | Umebayashi et al. |
| 8,361,047 B2 | 1/2013 | Mukai et al. |
| 2004/0078017 A1* | 4/2004 | Koyama ............ A61F 13/15203 604/378 |
| 2013/0110075 A1 | 5/2013 | Mukai et al. |
| 2013/0267924 A1* | 10/2013 | Mukai ................... A61F 13/533 604/374 |

FOREIGN PATENT DOCUMENTS

| | | |
|---|---|---|
| JP | 2002-320641 A | 11/2002 |
| JP | 2004-57413 A | 2/2004 |
| JP | 2004-141270 A | 5/2004 |
| JP | 2005-514244 A | 5/2005 |
| WO | 03/026545 A2 | 4/2003 |
| WO | 2006-118214 A1 | 11/2006 |
| WO | 2008/069279 A1 | 6/2008 |
| WO | 2011/132688 A1 | 10/2011 |

OTHER PUBLICATIONS

International Search Report mailed Apr. 23, 2013 in International Application No. PCT/JP2013/059261 filed Mar. 28, 2013.
Extended European Search Report dated Oct. 5, 2015, corresponding to European Patent Application No. 13769539.1.

* cited by examiner

FIG. 4
(a)
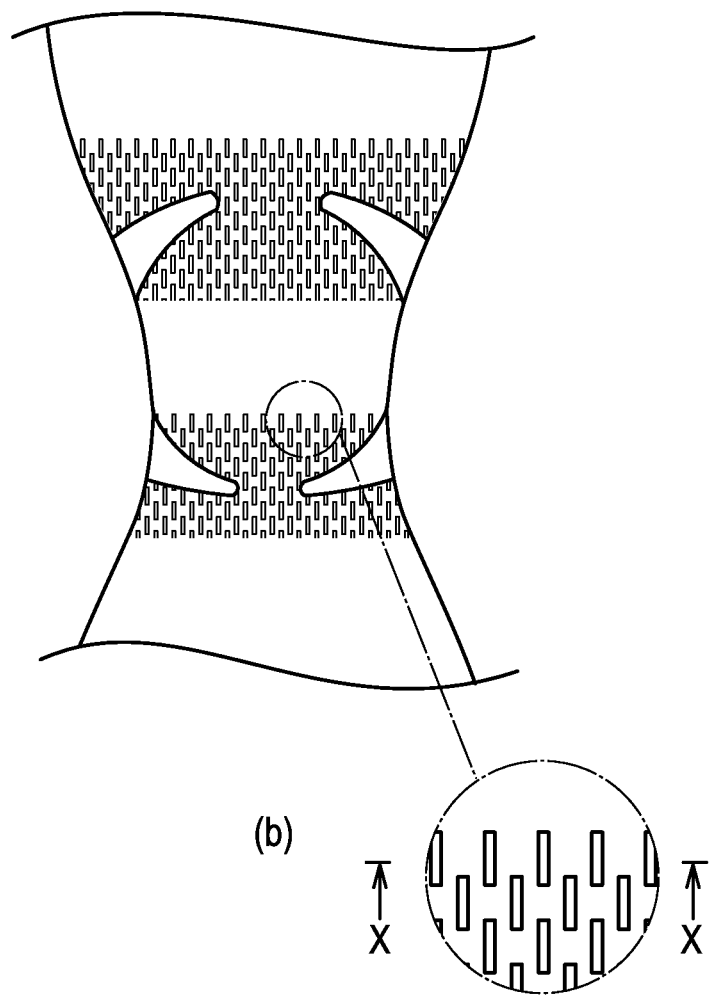
(b) 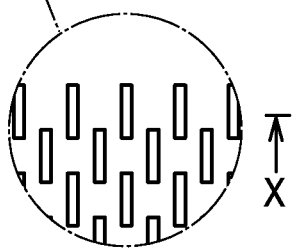
(c) 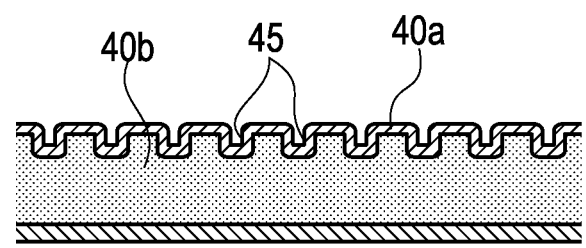

DISPOSABLE DIAPER

RELATED APPLICATIONS

The present application is a National Phase of International Application Number PCT/JP2013/059261, filed Mar. 28, 2013, which claims priority to Japanese Application Number 2012-081159, filed Mar. 30, 2012.

TECHNICAL FIELD

The present invention relates to a disposable diaper which is provided with a pair of leg hole openings and includes an absorber spanning a crotch region and extending to a front waistline region and a rear waistline region.

BACKGROUND ART

Conventionally, various disposable diapers have been devised to realize a good fit feeling while preventing leakage of bodily waste. For example, as for a disposable diaper including an absorber spanning a crotch region and extending to a front waistline region and a rear waistline region, there is known a configure in which the absorber is divided into three parts in the product longitudinal direction while elastic members in an extended state are arranged along the absorber at the outer side in the product widthwise direction of the absorber (for example, Patent Literature 1, FIGS. 1 and 2).

When the disposable diaper is worn, the space between the divided three parts of the absorber are narrowed to bring these parts in close contact with each other, thereby allowing the disposable diaper to fit into a wearer, so that the disposable diaper is prevented from sagging when the disposable diaper is worn.

CITATION LIST

Patent Literature

[PTL 1]
Japanese Unexamined Patent Application Publication No. 2004-141270

SUMMARY OF INVENTION

The conventional disposable diaper described above constantly exerts the force for bringing strongly the absorber in close contact with the body of a wearer, resulting from the contraction force of the elastic members arranged in an extended state along the absorber.

Therefore, the contraction force of the elastic members keeps exerting as force for sagging the front waistline region and the rear waistline region of the disposable diaper, downward in the direction of the crotch. Especially after the disposable diaper absorbs bodily waste, the front waistline region and the rear waistline region shift in the direction of the crotch, so that an unnecessary space is prone to be generated between a wearer and the disposable diaper.

Therefore, the present invention has been achieved in view of the above-described situation, and an object thereof is to provide a disposable diaper which is capable of following the body of a wearer without bringing the crotch region in too close contact while achieving reduction of an unnecessary space.

The disposable diaper (disposable diaper 10) according to the present disclosure is summarized as a disposable diaper including: a front waistline region (front waistline region 20); a rear waistline region (rear waistline region 30); a crotch region (crotch region 25) positioned between the front waistline region and the rear waistline region; an absorber (absorber 40) running across the crotch region and extending to the front waistline region and rear waistline region; a product longitudinal direction (product longitudinal direction L) from the front waistline region towards the rear waistline region; a product widthwise direction (product widthwise direction W) perpendicular to the product longitudinal direction; and a pair of leg hole openings (leg hole openings 35). The disposable diaper further includes: a pair of leg stretch units (leg stretch units 75) formed on a periphery of the leg hole openings and can expand and contract in at least the product longitudinal direction; and a crotch stretch (crotch stretch 200a) unit formed in an absorber arrangement region provided with the absorber within the crotch region, and can expand and contract in at least the product longitudinal direction. The absorber includes: a first region (first region 41) at least partially arranged in the crotch stretch unit; and a second region (second region 42) arranged adjacent to the first region at an outer side from the first region in the product longitudinal direction and having a lower bending rigidity than that of the first region; and a boundary between the first region and the second region is arranged at an outer side from an outer end of the crotch stretch unit in the product longitudinal direction and is arranged at an inner side from an outer end of the leg stretch unit in the product longitudinal direction.

BRIEF DESCRIPTION OF DRAWINGS

FIGS. 4a-4c are diagrams illustrating an absorber according to the present embodiment.

DESCRIPTION OF EMBODIMENTS

Figure 1:
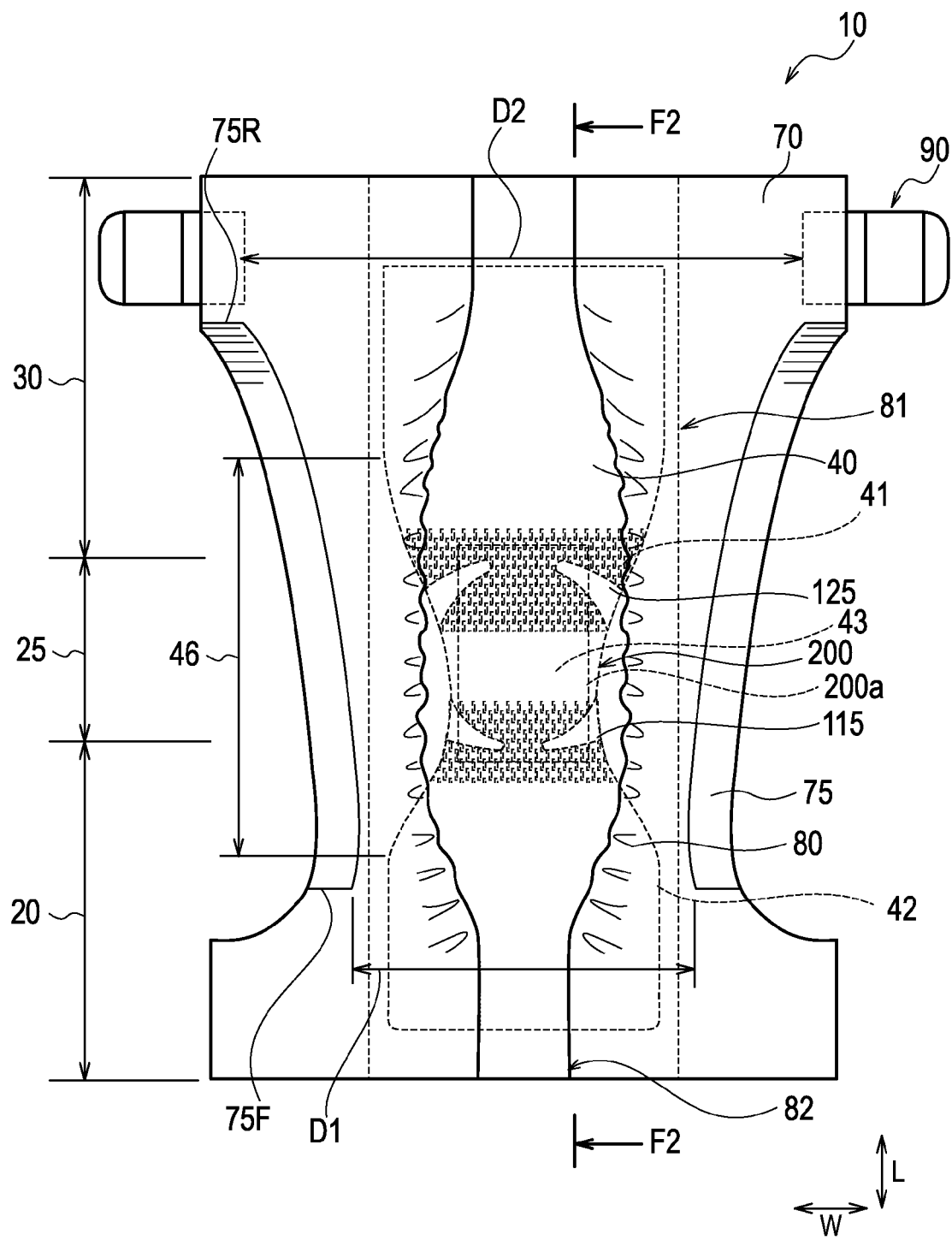
FIG. 1 is an exploded plan view of a disposable diaper according to a present embodiment.

Hereinafter, an embodiment of a disposable diaper according to the present invention is described with reference to accompanying drawings. In the following description of the drawings, the same or similar reference numerals are used to designate the same or similar units. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

(1) Overall Schematic Configuration of Disposable Diaper

Figure 2:
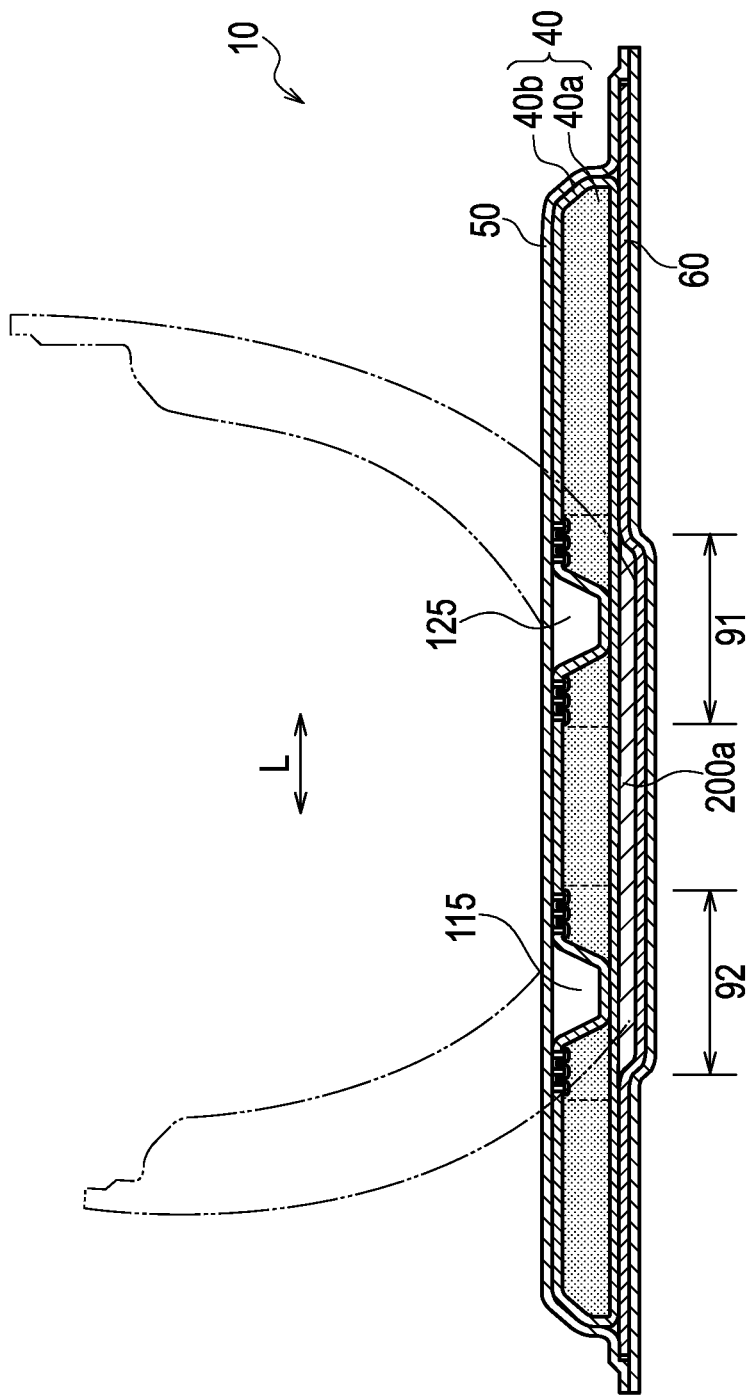
FIG. 2 is a cross-sectional view of the disposable diaper taken along the line F2-F2 line shown in FIG. 1.

FIG. 1 is an exploded plan view of a disposable diaper 10 according to the present embodiment. FIG. 2 is a cross-sectional view of the disposable diaper 10 taken along the line F2-F2 shown in FIG. 1. It should be noted that the exploded plan view of FIG. 1 is a diagram in which leg stretch units 75 and leg side gathers 80 are in an expanded state such that wrinkles are not formed in a topsheet 50 and side flaps 70, for example, that configure the disposable diaper 10, but for the sake of description, the leg side gathers 80 are illustrated in a contracted state.

The disposable diaper 10 has a front waistline region 20, a crotch region 25, and a rear waistline region 30. The front waistline region 20 is a part coming in contact with the front waistline portion (abdominal portion) of a wearer. Furthermore, the rear waistline region 30 is a part coming in contact with a rear waistline portion (dorsal portion) of a wearer. The crotch region 25 is positioned between the front waistline region 20 and the rear waistline region 30. Furthermore, the disposable diaper 10 is provided with a pair of leg hole opening 35 (see FIG. 5). The leg hole openings 35 are provided at side edges in the widthwise direction of the disposable diaper and are parts which are arranged along the leg holes of a wearer in a state in which the disposable diaper is worn by a wearer.

In the present embodiment, the direction from the front waistline region 20 towards the rear waistline region 30 is called the product longitudinal direction L, and the direction perpendicular to the product longitudinal direction L is called the product widthwise direction W.

The disposable diaper 10 includes an absorber 40 spanning the crotch region 25 and extending to the front waistline region 20 and the rear waistline region 30. The absorber 40 is made up of an absorbent core 40a and a core wrap 40b.

The absorbent core 40a is same as in the conventional disposable diaper, and can be configured appropriately by using popular components and materials, such as ground pulp and high absorbent polymer. The absorbent core 40a is wrapped in the sheet-like core wrap 40b. The core wrap 40b is a sheet for wrapping at least a part of the absorbent core 40a. A part of at least the skin surface contact side of the core wrap 40b is made from various fibrous nonwoven fabrics or a tissue sheet having liquid-permeability. For example, an air-through fibrous nonwoven fabric, a spunbond nonwoven fabric, or an SMS (spunbond-meltblown-spunbond) nonwoven cloth having a mass of approximately 10 to 30 g/m2, or a tissue sheet having a mass of approximately 10 to 30 g/m2 can be used.

A liquid-permeable topsheet 50 is provided at the top side (skin contact surface side) of the absorber 40. Furthermore, a liquid-impermeable backsheet 60a is provided at the back side (non-skin contact surface side) of the absorber 40.

Side flaps 70 are provided at side edges in the product widthwise direction W of the absorber 40, respectively. The side flap 70 is made of one or two or more pieces of nonwoven fabrics overlapping one another. Furthermore, the pair of side flaps 70 are provided with the fastening tapes 90, respectively.

The fastening tapes 90 extend in the product widthwise direction W in the rear waistline region 30 and are fixed to the non-skin contact surface side in the front waistline region to thereby retain the disposable diaper 10 to a wearer.

In the present embodiment, the front waistline region 20, the rear waistline region 30, and the fastening tapes 90 make up a front waistline retaining unit.

Furthermore, the disposable diaper 10 is formed in the crotch region 25 and includes a crotch stretch unit 200a which can expand and contract in the product longitudinal direction L. Specifically, the crotch stretch unit 200a is arranged in a crotch unit 200 formed in the crotch region 25. Configurations of the crotch unit 200 and the crotch stretch unit 200a are described later in details.

The top side (topsheet 50 side) of the absorber 40 is formed in the vicinity of the leg hole openings 35, and a pair of leg stretch units 75 which can expand and contract in the product longitudinal direction L are provided.

The leg stretch units 75 are longer in the product longitudinal direction L than the crotch stretch unit 200a while being provided at the outer side in the product widthwise direction W of the crotch stretch unit 200a.

As long as the leg stretch units 75 are configured to make the leg hole opening 35 can expand and contract e in the product longitudinal direction, the leg stretch units 75 may be arranged along the leg hole openings 35 or may be arranged with part of the leg stretch units 75 being inclined with respect to the leg hole openings 35.

Furthermore, the leg stretch units 75 are parts which are substantially contracted in the product longitudinal direction by means of a stretchable sheet or the like, and are a concept that excludes the part to which the stretchable sheet is arranged in a state in which no contraction force is exerted.

The leg stretch units 75 according to the present embodiment are made of stretchable members. For example, a stretchable film formed by melting a thermoplastic elastomer resin, such as urethane and styrene, and then converting into the shape of a film; a stretchable nonwoven fabric made from stretchable fibers; a composite sheet obtained by pasting an inextensible sheet partially cut or made fragile, to the stretchable film or the stretchable nonwoven fabric; or the like can be used as the aforementioned stretchable sheet.

Furthermore, in place of the stretchable sheet, the leg stretch units 75 may also be formed by arranging one or more thread-like or stripe-like elastic members made from polyurethane elastic fibers or natural rubber.

At least in the crotch region 25, a width (a width in the product widthwise direction W in of the disposable diaper 10 in a natural state) of the stretchable sheets making up the leg stretch units 75 is preferably 5 mm to 45 mm, more preferably 12.5 mm to 35 mm. In a case of a width smaller than 5 mm, the leg stretch units 75 follow the leg holes of a wearer by substantially using their surfaces, so that the fastening force does not concentrate partially, so that the elastic members cannot exhibit the effect of reducing the load on the skin. In a case of a width greater than 45 mm, a region following the leg holes widens too much in comparison to a length in the product widthwise direction of the entire disposable diaper, so that the stretchable sheets are easily caught on the body side of a wearer or turned up.

The ratio of expansion and contraction of the leg stretch units 75 is preferably 1.6 times to 2.4 times. In the present embodiment, the ratio of expansion and contractio of the leg stretch units 75 is set to 2.0 times.

It should be noted that the ratio of expansion and contraction of the leg gathers 75 is measured as described below.

The ratio of expansion and contraction of the leg gathers 75=(Length of the leg gathers 75 during maximum extension)/(Length of the leg gathers 75 in the natural state)

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the leg gathers 75 when the disposable diaper 10 is in the natural state, and the length of the leg gathers 75 when the disposable diaper 10 is extended from its natural state until wrinkles caused by the elastic members are not visible to the naked eye. The above measurement was performed for 10 samples, and the average value was assumed as the aforementioned length.

Hereinafter, the measurement of the "length" described in the specification will be performed based on the aforementioned measuring method.

Furthermore, the gap between the inner ends of the pair of right-left leg stretch units 75 in the product widthwise direction W widens from the crotch region 25 towards the front waistline region 20, and also widens from the crotch region 25 towards the rear waistline region 30. By arranging the leg stretch units in a shape that is narrowed in the crotch portion and widened towards the front and rear waistlines, the leg stretch units can follow a line of the body, thereby being able be suitably arranged in an extended state around the leg holes of a wearer.

Further, the gap (D1 in the drawings) between the pair of right-left leg stretch units 75 at the end of the front waistline region 20 is smaller than the gap (D2 in the drawings) between the pair of right-left leg stretch units 75 at the end of the rear waistline region 30. It should be noted that these gap are obtained by measuring a distance between the inner ends in the product widthwise direction W of the pair of right-left leg stretch units 75 after the disposable diaper 10 is shifted from the natural state to a state free from wrinkles by stretching out and retaining the disposable diaper 10 in the product longitudinal direction L and the product widthwise direction W.

A stretch of the skin surface of the body of a wearer is large especially in the hip portion and stands out in a position closer to the outer side in the widthwise direction of the hip portion. Furthermore, the leg stretch units 75 are in close contact with the body of a wearer. Thus, with a configuration of D2>D1, even in a case where the disposable diaper 10 is given a movement of a wearer, the leg stretch units 75 at the hip portion side can be stretched out while keeping tight contact, so that the leg stretch units 75 are not projected even if the stretch has the large amount of change. Accordingly, it is possible to prevent shifting of the disposable diaper 10 due to the leg stretch units 75.

Further, a pair of leg side gathers 80 extending in the product longitudinal direction L are provided in the inner side (closer to the center in the product widthwise direction W) of the pair of leg stretch units 75. The leg side gathers 80 are provided at the inner ends in the product widthwise direction of the side flaps, and are orthostatic stretch gathers arranged at the inner side in the product widthwise direction of the leg stretch units. Each of the side flaps is folded over towards the topsheet side at the inner end in the product widthwise direction to form a lamination of two layers. An elastic member 76 (see FIG. 2) is provided in an extended state in the longitudinal direction, between the two layers of the side flap. This side flap 70 and the elastic member 76 form the leg side gather 80.

Each of the leg side gathers 80 has a joining part 81 to be joined to a backsheet 60a, and a free end portion 82 positioned at the opposite side of the joining part 81 and provided with an elastic member (not shown in FIG. 1). As for the leg side gather 80, when the diaper is worn, the joining part 81 rises up as the proximal end and the free end portion 82 comes in contact with the skin of a wearer as the apex.

It should be noted that the backsheet 60a is arranged between the absorber 40 and an exterior sheet 60 and functions as a leakage-preventing sheet.

Furthermore, the end in the product longitudinal direction L of the free end portion 82 of the leg side gather 80 is joined to the topsheet 50. The joining part 81 is arranged between the crotch stretch unit 200a and the leg stretch unit 75 in the product widthwise direction W.

The joining part 81 of the leg side gather 80 can adopt various configurations. For example, the joining part may be a part extending in the product longitudinal direction from the crotch unit to the front waistline region and the rear waistline region and joined to the topsheet, or may be a part joined to the liquid-impermeable backsheet or the exterior sheet at the outer side in the widthwise direction of the absorbent core 40a, and is configured as the proximal end of rising.

Furthermore, as long as the leg side gather is an orthostatic gather arranged at the inner side in the product widthwise direction of the leg stretch unit, its configuration is not limited to the above, and it goes without saying that the conventionally known configuration of the leg side gather can be adopted.

It should be noted that the disposable diaper 10 may include the waist side gathers arranged in the product widthwise direction W in the front waistline region 20 and the rear waistline region 30. A structural member of the waist gathers is not particularly limited, but preferably used is a member having a thickness as small as possible, a low bending rigidity, and a small width reduction rate, such as a stretch film.

(2) Shape of Crotch Unit

Figure 3:
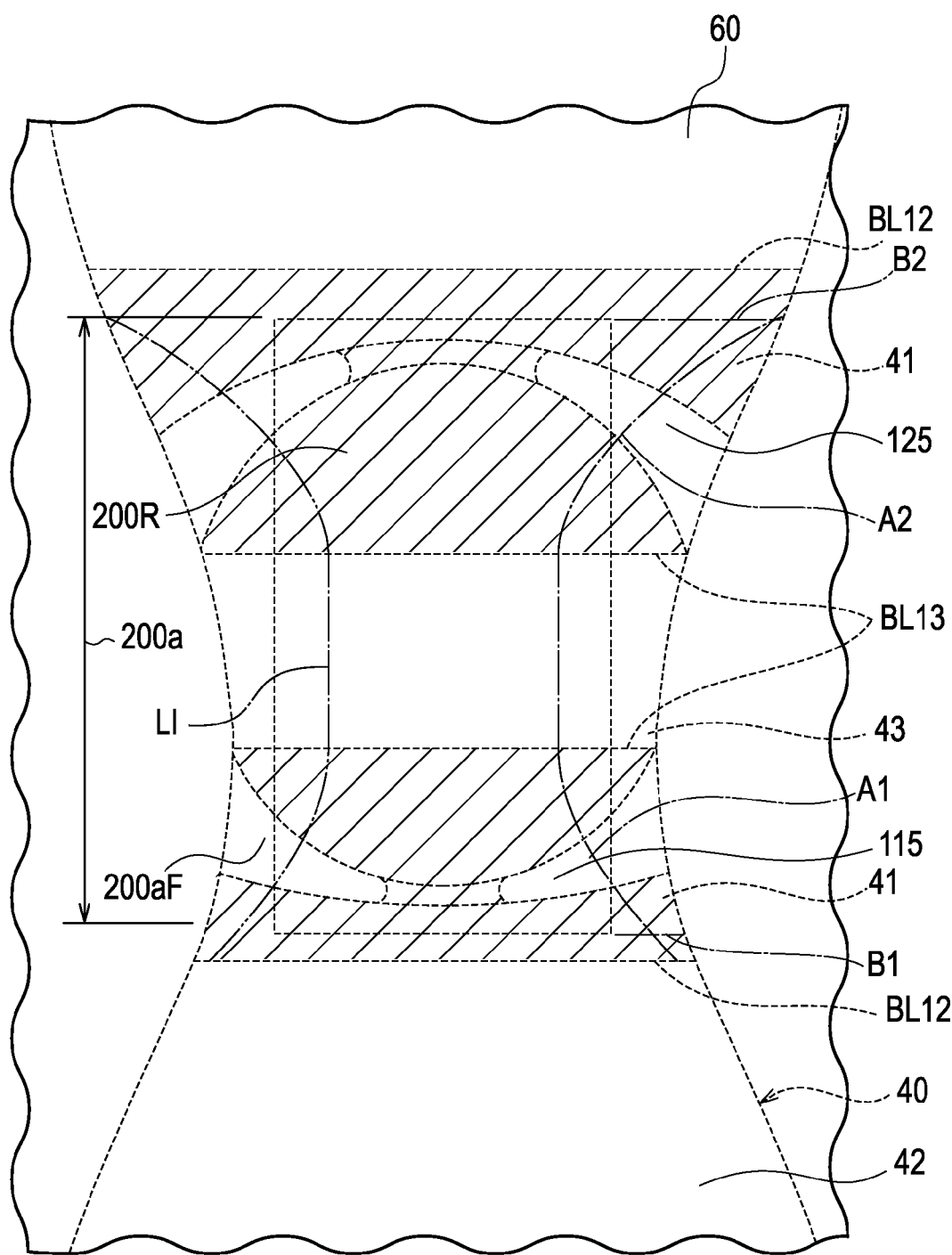
FIG. 3 is an enlarged plan view of a crotch unit according to the present embodiment, as seen from a backsheet side.

Next, the shape of the crotch unit 200 is explained. FIG. 3 is an enlarged plan view of the crotch unit, as seen from the backsheet side. As described above, the crotch unit 200 has the crotch stretch unit 200a. The crotch stretch unit 200 is configured so as to make it easy for the absorber 40 to keep its shape which is more flat than the other parts when the disposable diaper is worn. The crotch unit 200 includes the crotch stretch unit 200a which can expand and contract at least in the product longitudinal direction L or the product widthwise direction W.

The crotch stretch portion 200a is provided individually and independently of the leg stretch units 75, and is configured, in a position overlapped with the absorbent core 40a (in the present embodiment, a position between the core wrap 40a wrapping the absorbent core 40a and the backsheet 60a), so as to cause contraction by 60% or more of a length in the widthwise direction of the absorbent core 40a in the aforementioned overlapping position. As described above, by contracting the portion provided with the absorbent core 40a by means of the crotch stretch unit 200a, the absorbent core 40a is contracted, thereby easily keeping the flat shape as compared to the part in which the absorbent core 40a is not contracted.

On the other hand, the absorbent core 40a positioned in the front waistline region or the rear waistline region positioned at the outer side in the product longitudinal direction of the crotch stretch unit 200a is not contracted by means of the crotch stretch unit 200a, so that the crotch unit 200 is arranged along the body to a moderate degree without bringing the entire absorber in too tight contact with the body.

Furthermore, the crotch unit 200 can expand and contract in the product longitudinal direction L, which makes it easy for the front waistline region 20 and the rear waistline region 30 to rise up in association with contraction of the crotch unit 200, thereby forming the flat crotch region along the body at the crotch of a wearer when the diaper is worn. The front waistline region and the rear waistline region rise up from the crotch stretch unit 200a, thereby improving the fitting property of the disposable diaper 10 into a wearer. The crotch stretch unit 200a is preferably made from the stretchable sheet. By making the crotch stretch unit 200a from the stretchable sheet, the absorbent core 40a in the region provided with the stretchable sheet is uniformly contracted, thereby making it easy to keep the flat shape. The stretchable sheet can be made from the same as that of the leg stretch unit 75, for example.

Furthermore, in place of the stretchable sheet, the crotch stretch portion 200a may also be configured by arranging one or more thread-like or stripe-like stretchable elastic members made from polyurethane elastic fibers or natural rubber. In such a case, in order to uniformly contract the absorbent core 40a by means of the crotch stretch unit 200a, an gap between the elastic members is set to preferably 7 mm or less, more preferably 5 mm or less. For the purpose of uniform contraction of the absorbent core 40a, a difference in the gap between adjacent elastic members is desirably 0.5 mm or less.

Furthermore, the ratio of expansion and contraction of the crotch stretch unit 200a is preferably 1.2 times or more and 1.8 times or less, specifically. In the present embodiment, the ratio of expansion and contraction of the crotch stretch unit 200a is set to 1.4 times.

The ratio of expansion and contraction of the crotch stretch unit 200a implies the extent of the expansion and contraction of the crotch stretch unit 200a in the direction of expansion and contraction (product longitudinal direction L), and is stipulated as below:

The ratio of expansion and contraction of crotch stretch unit 200a=(Length of the crotch unit during maximum extension)/(Length of the crotch unit in the natural state). It should be noted that the ratio of expansion and contraction as used herein is to be measured as described below, for example.

Firstly, in a case where the disposable diaper 10 is inserted in a package, for example, then the disposable diaper 10 is taken out of the package, and the diaper is kept in such a condition for 60 minutes in an ambient atmosphere having a temperature of 20° C.±2° C., and a relative humidity of 60%±5% RH, and then a length of the crotch stretch unit is measured i in the direction of expansion and contraction. This length is set to a "length i in the direction of expansion and contraction of the crotch stretch unit 200a in the natural state".

Secondly, measurement is performed with respect to the length in the direction of expansion and contraction of the desired region in this state (that is, in the natural state), and the length in the direction of expansion and contraction of the desired region when the disposable diaper is extended from its natural state to a state in which wrinkles caused by the elastic members cannot be visually confirmed. This length is set to a "length in the direction of expansion and contraction of the crotch stretch unit 200a in the maximum extended state".

As described above, by setting the ratio of expansion and contraction of the crotch stretch unit 200a to 1.2 times to 1.8 times, it is possible to favorably follow the stretching of the skin of the wearer.

For example, when the wearer is slouchy such that the front side of the body is cringing, in the skin at the side of the hip portion of the wearer, there is a region that stretches by approximately 30% as compared to the state when the body has been stretched out.

That is, when the ratio of expansion and contraction of the crotch stretch unit 200a is 1.2 times or less, the contraction of the crotch stretch unit 200a in the natural state is insufficient, and as compared to the case where the crotch stretch unit 200a has not been provided, the difference in the ease of curving of the disposable diaper 10 is small because of which the front waistline region 20 does not rise at the desired position.

On the other hand, when the ratio of expansion and contraction of the crotch stretch unit 200a is more than 1.8 times, the contraction size in the contraction direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the center in the product longitudinal direction L of the crotch stretch unit 200a is arranged closer to the front waistline region 20 side as compared to the center in the product longitudinal direction L of the disposable diaper 10. However, the crotch stretch unit 200a is arranged so as to span the center in the product longitudinal direction L of the disposable diaper 10.

In such a case, in view of the rigidity of the absorbent core 40a and the rigidity of other members configuring the disposable diaper 10, the thickness of the elastic members and the arrangement pitch can be selected appropriately. However, when the main body of the disposable diaper 10 is in the natural state (unextended state), the entire side edge in the product widthwise direction W of the absorbent core 40a is preferably in a contracted state.

Furthermore, the crotch region 25 of the absorber 40 is provided with a notch 115 (notch 125). The notches 115, 125 are regions without having the absorbent core 40a making up the absorber 40. In the present embodiment, the notches 115, 125 correspond to a low rigidity unit having a smaller basis weight of the absorbent core 40a than the other parts of the absorbent core 40a. It should be noted that instead of formation of the notches 115, 125, the regions of the notches 115, 125 may be configured to have a smaller basis weight of the absorbent core 40a than the other parts of the absorbent core 40a.

The notches 115, 125 exist along the edges in the product longitudinal direction L of the crotch unit 200. Even with the formation of the notches 115, 125, the absorbent core 40a positioned in the front waistline region 20 and the rear waistline region 30 is preferably continuous to the absorbent core 40a positioned in the crotch region 25 without complete separation, especially in the widthwise direction.

The length in the product longitudinal direction L of the notches 115, 125 widens towards the outer side in the product widthwise direction W. With such a shape, the outer side in the widthwise direction W of the absorbent core 40a is contracted more easily, thereby making it easier to form the flat "bottom". Furthermore, the absorbent core 40a positioned closer to the front waistline region 20 than the notch 115 and the absorbent core 40a positioned closer to the rear waistline region 30 than the notch 125 rise up from the "bottom" and are prone to be curved along the roundness of the body (abdominal portion and hip portion) of a wearer, so that the disposable diaper itself can be shaped more like the shape of the body of a wearer.

Furthermore, the edge closer to the front waistline region 20 (rear waistline region 30) of the notch 115 (notch 125) is arc-shaped. The edge of the notch 115 (notch 125) is shaped so that the center of the arc is positioned closer to the rear waistline region 30 (front waistline region 20) as compared to the edge itself. Such a shape realizes the deformation along the roundness of the body of a wearer more easily and prominently.

(3) Shape of Crotch Unit

Next, the shape of the absorber 40 is explained. FIG. 4 is a diagram illustrating the absorber. FIG. 4(a) is an enlarged plan view as seen from the topsheet 50 side, FIG. 4(b) is a partially enlarged view of FIG. 4(a), and FIG. 4(c) is an X-X cross-sectional view of FIG. 4(b).

The absorber 40 includes a first region 41 at least partially arranged in the crotch stretch unit 200a, and a second region 42 arranged adjacent to the first region 41 at the outer side in the product longitudinal direction of the first region 41 (at the front waistline region side or the rear waistline region side) and having a lower bending rigidity than the first region 41.

The first region 41 of the absorber 40 is provided at two places with an gap in the product longitudinal direction. One first region 41 is arranged so as to overlap with an end 200Af (see FIG. 1) at the front waistline region side of the crotch stretch unit while the other first region 41 is arranged so as to overlap with an end 200aR (see FIG. 1) at the rear waistline region of the crotch stretch unit. The absorber 40 is arranged at the inner side in the product longitudinal direction of the first region 41 (between the first regions 41 at two places) and has a third region 43 having a lower bending rigidity than the first region 41.

The first region 41 is provided in the entire absorber in the product widthwise direction. The first region 41 is provided with a compressed unit 41 in which the absorber 40 is compressed in the product thickness direction. A plurality of compressed units 45 are formed intermittently across the entire first region 41. On the other hand, the second region 42 and the third region 43 are not provided with any compressed unit 45. Therefore, the first region 41 is configured to have a higher bending rigidity than those of the second region 42 and the third region 43.

The bending rigidity in the present embodiment is based on a rigidity value in accordance with the taber method (JISP8125), and it can be confirmed by the measurement based on the following method. First, from the disposable diaper in the expanded state, a sample (for example, the absorber) of an object part for measuring a bending rigidity is collected. The sample is prepared for the measuring object part, in a size having a sample length of 70 mm in the product widthwise direction or the product longitudinal direction and a length of 38 mm in the widthwise direction perpendicular to the sample length direction. In a case where the sample contains a stretch elastic member therein, the elastic member is removed beforehand. It should be noted that as a tester for measuring a rigidity value, a taber stiffness tester manufactured by Yasuda Seiki Seisakusho, Ltd., is used. Furthermore, the number of samples is ten, in which each of the samples is measured and an average value is set as a rigidity value.

The measurement procedure is shown by the following (a) to (e).

(a) Thickness (A) of the collected sample is measured.

(b) Subsequently, the sample is sandwiched to an extent that it comes in contact with the center of a zipper (lower side) of the tester.

(c) Adjustment is made so that a total of right-left gaps between a supporting roller and the sample is set to (A)×0.80 (mm)

(d) An auxiliary weight is appropriately selected so that the designed load scale falls within 15 to 85% of the maximum scale.

(e) The sample is rotated in right and left directions and is stopped at the point that 15 degrees marking line and the center mark of the pendulum correspond to each other, and the scale of the tester is read. A numerical value at the left side of the scale is set as (B) while a numerical value at the right side of the scale is set as (C).

A rigidity value is obtained by the following expression.

$$\text{Rigidity value (mN·m)} = ((B)+(C))/2) \times (\text{Auxiliary weight coefficient}) \times 9.81 \times 10^{-2}$$ Expression:

In a case where a width of the test piece cannot collect in a size of 38 mm, a conversion to a bending moment with a width of 38 mm is performed.

As the rigidity value thus measure is larger, the bending rigidity is higher, while the rigidity value is smaller, the bending rigidity is lower.

The plurality of compressed units 45 are configured so that the length in the product longitudinal direction is larger than the length in the product widthwise direction, and they are arranged in a staggered form. As described above, the compressed units 45 are discontinuously arranged in the staggered form, so that a compressed part and a non-compressed part are mixed in the first region 41. The non-compressed part has the lower bending rigidity than that of the compressed part, thereby being deformable flexibly, which makes it possible to improve the bending rigidity of the first region 41 while arranging the first region 41 along a line of a curvy body.

The compressed unit 45 may be formed while being compressed in the thickness direction from the outer side of the core wrap 40b in a state in which the absorbent core 40a is wrapped in the core wrap 40b, or may be formed by making formation so that the absorbent material of the first region 41 has a higher basis weight than that of the absorbent material of the second region 42 at the time of laminating the absorbent materials making up the absorbent core 40a, and by compressing the absorbent core 40a in the thickness direction.

Furthermore, the absorber according to the present embodiment is configured so that the bending rigidity of the first region 41 is made high by formation of the compressed units 45. However, other configuration may be adopted to configure the absorber so that the bending rigidity of the first region 41 is made higher than those of the second region 42 and the third region 43.

The boundary between the first region 41 and the second region 42 and the boundary between the first region 41 and the third region 43 are arranged in the product widthwise direction W. FIG. 3 shows a boundary line BL12 virtually showing the boundary between the first region 41 and the second region 42, and a boundary line BL13 virtually showing the boundary between the first region 41 and the third region 43.

The boundary between the first region 41 and the second region 42 is arranged in each of the front waistline region 20 and the rear waistline region 30, and arranged at the outer side in the product longitudinal direction of the outer end of the crotch stretch unit in the product longitudinal direction and at the inner side in the product longitudinal direction of the outer end of the leg stretch unit in the product longitudinal direction.

Specifically, the boundary between the first region 41 and the second region 42 in the front waistline region is arranged closer to the front waistline region side than an end 200aF at the front waistline region side of the crotch stretch unit 200a and closer to the rear waistline region side than an end 75F (see FIG. 1) at the front waistline region side of the leg stretch unit 75. Furthermore, the boundary between the first region 41 and the second region 42 in the rear waistline region is arranged closer to the rear waistline region side than an end 200aR at the rear waistline region side of the crotch stretch unit 200a and closer to the front waistline region side than an end 75R (see FIG. 1) at the rear waistline region side of the leg stretch unit 75.

The boundary between the first region 41 and the second region 42 is a part in which the absorber 40 has a different bending rigidity, and is an inflecting part in which the absorber is easily bent. Therefore, at the time of application of external force for deforming the absorber, the absorber can be easily deformed with the boundary between the first region 41 and the second region 42 as a base point.

As described above, the crotch region 25 is pulled up towards a wearer's side by means of the crotch stretch unit 200a which is contracted at least in the product longitudinal direction. Therefore, the crotch unit 200 is arranged in a position close to a wearer. Accordingly, the absorber 40 can be easily arranged along the position close to the body even in a case where a weight or load is applied from outside.

Furthermore, the crotch stretch unit 200a is contracted at least in the product longitudinal direction, thereby having a higher bending rigidity as compared to the periphery which is not contracted. Thus, the boundary between the crotch stretch unit 200a and its periphery functions as an inflection point because of a rigidity difference. Therefore, the inflection point is arranged at each end in the longitudinal direction of the crotch stretch unit 200a, thereby causing a deformation so that the crotch stretch unit is set as the bottom.

The crotch stretch unit 200a positioned in the crotch region 25 forms the bottom, and can be arranged so as to face to the crotch of a wearer. Furthermore, the parts closer to the front waistline region side and the rear waistline region side than the crotch stretch unit has a lower bending rigidity than that of the crotch stretch unit, and can be arranged along the abdominal side and the dorsal side of a wearer.

Furthermore, the first region and the second region each of which has a different bending rigidity are provided in the absorber 40. The first region 41 is arranged from the crotch stretch unit 200a to the outer side in the product longitudinal direction (the front waistline region side or the rear waistline region side), and the second region 42 is arranged at the outer side in the product longitudinal direction of the first region 41. The boundary between the first region 41 and the second region 42 is arranged by being shifted towards the outside in the product longitudinal direction of each end in the product longitudinal direction of the crotch stretch unit.

By a combination of the crotch stretch unit 200a and the first and second regions 41, 42, the plurality of inflection points causing a rigidity difference are formed to deform the absorber in stages, thereby realizing the smooth inflection. For example, a bending rigidity of the first region provided with the crotch stretch unit is higher than that of the first region not provided with the crotch stretch unit, and a bending rigidity of this first region not provided with the crotch stretch unit is higher than that of the second region.

Figure 5:
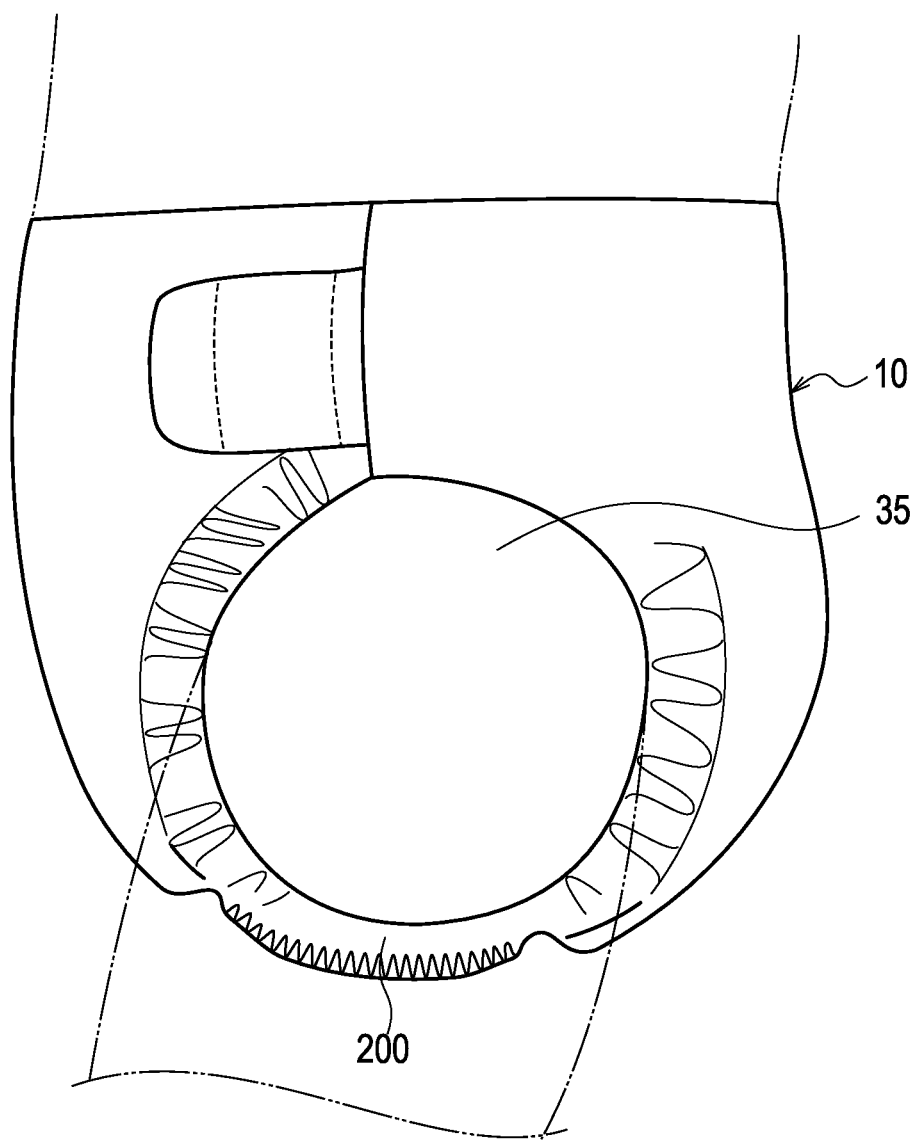
FIG. 5 is a diagram illustrating schematically a state in which the disposable diaper according to the present embodiment is worn by a wearer.

FIG. 5 is a diagram illustrating schematically a state in which the disposable diaper according to the present embodiment is worn by a wearer. For convenience of explanation, FIG. 5 illustrates schematically the first region 41 and the third region 43 of the absorber arranged inside the disposable diaper. The absorber 40 is provided with regions having different bending rigidities at least in three stages, which makes it possible to arrange the disposable diaper along the body with a better fit, thereby achieving reduction of an unnecessary space.

Furthermore, each outer end in the product longitudinal direction of the crotch stretch unit 200a is positioned inside the first region having a relatively high bending rigidity, thereby preventing a sharp inflection of each end of the crotch stretch unit 200a, realizing a smooth deformation of the absorber 40.

Furthermore, the absorbent core 40a of the absorber has a narrow region 46 shaped concave towards the inner side in the widthwise direction so that a length in the product widthwise direction of the crotch region is set shorter than those in the product widthwise direction of the front waistline region and the rear waistline region. An end 41F at the front waistline region side and an end 41R at the front waistline region side as the outer ends in the longitudinal direction of the first region 41 are positioned inside the narrow region 46 of the absorber.

The narrow region 46 in the front waistline region is a region supposed to be inflected smoothly along the body's line so that the disposable diaper 10 extends from the abdominal side waistline toward the crotch portion of a wearer. By providing this narrow region 46 with the first region 41 at least part of which is overlapped with the crotch stretch unit 200a, the curved line can be formed smoothly between the crotch stretch unit 200a to the hipline at the front waistline region side. It should be noted that the first region is required only to extend longer by 40 mm to 10 mm at the outer side in the longitudinal direction than the crotch stretch end in the product longitudinal direction, and more preferably by 30 mm to 15 mm at the outer side in the longitudinal direction.

Furthermore, each outer end in the longitudinal direction of the first region is located at the inner side in the longitudinal direction of each end in the longitudinal direction of the leg stretch unit, and the first region is positioned in the longitudinal direction within the region in which the leg stretch unit is arranged. The region in which the leg stretch unit is arranged is a region supposed to deform smoothly from the abdominal portion or the hip portion towards the crotch region. The first region has a relatively high bending rigidity, which prevents a local deformation, thereby enabling the absorber to be arranged in a smoothly curved form.

Furthermore, the third region 43 having a lower bending rigidity than that of the first region 41 is provided between the first regions 41 in the product longitudinal direction. Out of these boundaries between the first regions 41 and the third region 43, the boundary positioned at the front waistline region side extends in the widthwise direction by passing through the inner end in the product longitudinal direction of the notch 115, and arranged closer to the rear waistline region side than the end 200aF at the front waistline region side of the crotch stretch unit. Furthermore, out of these boundaries between the first regions 41 and the third region 43, the boundary positioned at the rear waistline region side extends in the widthwise direction by passing through the inner end in the product longitudinal direction of the notch 125, and arranged closer to the front waistline region side than the end 200aR at the rear waistline region side of the crotch stretch unit.

In the plan view of the disposable diaper, a part of the first regions 41 and the third region 43 are arranged in the region overlapping with the crotch stretch unit 200a. The crotch unit 200 is a part to which the force towards the inner side in the widthwise direction is applied by the legs or the like of a wearer. When the crotch unit 200 is sandwiched between both legs, the inner line LI in the widthwise direction of the legs sometimes reaches the position shown in FIG. 3. As described above, in a case where the leg reaches the inner line LI, the third region 43 of the absorber 40, which has a relatively low bending rigidity to realize easy deformation, deforms so as to rise up towards a wearer's side. Furthermore, the first regions 41 at the outer side in the product longitudinal direction of the third region 43 have arrangement of the crotch stretch nit 200a and is in a contacted state in the product longitudinal direction, thereby deforming so as to rise up towards a wearer's side in association with the deformation of the third region 43. As described above, propagation of the deformation of the absorber 40 towards the outer side in the product longitudinal direction causes the part having arrangement of the crotch stretch unit 200a to deform so as to rise up towards a wearer's side based on a region B1 extending in the widthwise direction from the end at the front waistline region side of the crotch stretch unit 200a and a region B2 extending in the widthwise direction from the end at the rear waistline region side of the crotch stretch unit 200a. Accordingly, the crotch unit 200 deforms along line A1 in a curved form extending from the ends in the product widthwise direction of the region B1 towards the inner line and line B2 in a curved form extending from the ends in the product widthwise direction of the region B2 towards the inner line. such deformation of the crotch unit in the enables the disposable diaper to be arranged by being inflected in an appropriate shape in the crotch region 25 arranged in the part having the smallest gap between the legs of a wearer, so that the disposable diaper follows the body in a more suitable state, thereby making it easy for a wearer to move.

(4) Operation and Effect

The absorber 40 is provided with the first regions having a relatively high bending rigidity and the second region having a relatively low bending rigidity, and the first region 41 is arranged at the outer side in the product longitudinal direction of the crotch stretch unit 200a (at the front waistline region side or the rear waistline regions side), so that by a combination of the crotch stretch unit 200a, the first region 41, and the second region 42, the plurality of inflection points causing a rigidity difference are formed to enable the absorber to deform in stages to be inflected smoothly. The absorber is provided with regions having a different bending rigidity at least in three stages, which makes it possible to arrange the disposable diaper along the body with a better fit, thereby achieving reduction of an unnecessary space.

Furthermore, the plurality of compressed units of the disposable diaper 10 are formed intermittently across the entire the first region. Thus, a bending rigidity can be made substantially equally high in the entire first region. Furthermore, in the first region, the plurality of compressed units are arranged intermittently in the first region, so that the compressed part and the non-compressed part are mixed in the first region. The non-compressed part has a lower bending rigidity than that of the compressed part, thereby being deformable flexibly, which makes it possible to improve the bending rigidity of the first region 41 while arranging the first region 41 along a line of a curvy body.

Furthermore, since the notches 115, 125 as low rigidity units are provided in the absorber, these low rigidity units function as inflection points, which enhances the deformation of the absorber. Furthermore, the low rigidity units are projected to the outer side in the product longitudinal direction of the crotch stretch unit. Thus, the front waistline region and the rear waistline region at the outer side in the product longitudinal direction of the crotch stretch unit are easily risen up towards a wearer's side in a state in which the crotch stretch unit forms the bottom. Accordingly, the absorber can be easily arranged along the body with a better fit.

Furthermore, the first regions 41 are provided with the notches 115, 125 as low rigidity units. For example, by a combination of the notch and the crotch stretch unit 200a, the deformation of the absorber 40 along the roundness of the body can be formed in only the front waistline region, only rear waistline region, or both the front waistline region and the rear waistline region.

Furthermore, in the notches 115, 125, the absorbent core does not exist or has a low basis weight, so that the absorber 40 is easily gets out of shape and hardly keeps its shape in the periphery of the notches 115, 125. However, by providing the notches 115, 125 in the first regions, the rigidity of the periphery of the notches 115, 125 can be increased to make it easy for the absorber 40 to keep its shape.

Furthermore, the crotch stretch unit is provided with the first regions and the third region, resulting in more inflection points in the crotch stretch unit, thereby making it easy for the absorber to be arranged along the body with a better fit. The center in the product longitudinal direction of the crotch stretch unit is arranged so as to be close to the excretion portion of a wearer, and is a part which is easily sandwiched between both legs. By arrangement of the third region 43 in the approximate center in the product longitudinal direction of the crotch stretch unit 200a, the resistance can be reduced at the time of sandwiching the approximate center between the legs. Furthermore, since the third region 43 having a relatively low bending rigidity is sandwiched between the legs, the stimulation on the skin can be prevented while the bottom made up of the crotch stretch unit 200a can be formed in a shape which is more suitable to the body.

(4) Other Embodiments

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

For example, in the absorber according to the above-described embodiment, the plurality of first regions of the absorber are formed at an interval and the third region is provided there between. However, the absorber according to the present invention may not include the third region while the first regions may be provided continuously.

Furthermore, in the above-described embodiment, the open-type disposable diaper provided with has been described as an example. However, the present invention can also be applied to a pant-type disposable diaper. In the pant-shaped diaper, which has a waistline opening and a pair of leg hole openings by joining together both right-left side edges of the exterior layer sheet making up the front waistline region and the rear waistline region, the exterior layer sheet I the front waistline region and the rear waistline region includes elastic elements which is contractible and extendable in the product widthwise direction W, and the disposable diaper is retained along the waistline of a wearer by contracting these elastic elements. That is, the range in which the right-left side edges extending in the product longitudinal direction L are joined together, functions as a waistline retaining unit. Furthermore, in the disposable diaper according to the modification, rather than leg gathers formed from an elastic nonwoven sheet, leg gathers formed from thread-like elastic members may be provided.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2012-081159 (filed on Mar. 30, 2012) are incorporated in the present specification by reference.

INDUSTRIAL APPLICABILITY

It is possible to provide a disposable diaper which is capable of following the body of a wearer without bringing the crotch region in too close contact while achieving reduction of an unnecessary space.

The invention claimed is:

1. A disposable diaper, comprising:
   a front waistline region;
   a rear waistline region;
   a crotch region positioned between the front waistline region and the rear waistline region;
   an absorber running across the crotch region and extending to the front waistline region and rear waistline region;
   a product longitudinal direction from the front waistline region towards the rear waistline region;
   a product widthwise direction perpendicular to the product longitudinal direction;
   a pair of leg hole openings;
   a pair of leg stretch units formed on a periphery of the leg hole openings and expandable and contractible in at least the product longitudinal direction; and
   a crotch stretch unit formed within the crotch region, and expandable and contractible in at least the product longitudinal direction,
   wherein
   each of the leg stretch units has front and rear ends opposing each other in the product longitudinal direction,
   the crotch stretch unit has front and rear ends opposing each other in the product longitudinal direction,
   the crotch stretch unit is arranged, in the product longitudinal direction, between the front and rear ends of each of the leg stretch units,
   the absorber includes:
      a first region overlapping the crotch stretch unit in a product thickness direction; and
      a second region arranged adjacent to the first region in the product longitudinal direction and having a lower bending rigidity than that of the first region, and
   a boundary between the first region and the second region is arranged, in the product longitudinal direction,
      either (i) between the front end of the crotch stretch unit and the front end of each of the leg stretch units,
      or (ii) between the rear end of the crotch stretch unit and the rear end of each of the leg stretch units;
   wherein longitudinally extending side edges of the absorber each include a notch that overlaps the crotch stretch unit.

2. The disposable diaper according to claim 1, wherein the absorber has a compressed unit compressed in the product thickness direction and formed in the first region.

3. The disposable diaper according to claim 2, wherein a plurality of the compressed units are formed intermittently across an entirety of the first region.

4. The disposable diaper according to claim 1, wherein the absorber includes an absorbent core and a core wrap covering at least a part of the absorbent core,
   the absorber is provided with a narrow region having a width in the product widthwise direction gradually decreasing from the front and rear waistline regions toward the crotch region in the product longitudinal direction,
   the width of the absorbent in the product widthwise direction at the crotch region is smaller than widths of the absorber in the front and rear waistline regions in the product widthwise direction, and
   the crotch stretch unit overlaps the narrow region in the product thickness direction.

5. The disposable diaper according to claim 1, wherein
   the absorber includes an absorbent core and a core wrap covering at least a part of the absorbent core,
   the absorber is provided with a narrow region having a width in the product widthwise direction gradually decreasing from the front and rear waistline regions toward the crotch region in the product longitudinal direction,
   the width of the absorbent in the product widthwise direction at the crotch region is smaller than widths of the absorber in the front and rear waistline regions in the product widthwise direction, and
   the boundary between the first region and the second region is arranged inside the narrow region.

6. The disposable diaper according to claim 1, wherein
   the notches correspond to a low rigidity unit that has no absorbent core making up the absorber, or has a lower basis weight than that of a remaining part of the absorber, in a region overlapping the crotch stretch unit in the product thickness direction.

7. The disposable diaper according to claim 6, wherein the low rigidity unit is provided in the first region.

8. The disposable diaper according to claim 1, wherein
   the absorber further includes a third region adjacent to the first region in the product longitudinal direction, said third region having a lower bending rigidity than that of the first region,
   the crotch stretch unit has a center in the product longitudinal direction, and
   the third region overlaps the center of the crotch stretch unit in the product thickness direction.

9. The disposable diaper according to claim 1, wherein
   the first region has a front end, and
   a distance between the front end of the first region and the front end of the crotch stretch unit is 15 mm to 30 mm.

10. The disposable diaper according to claim 1, wherein the first region of the absorber overlaps the front and rear ends of the crotch stretch unit in the product thickness direction.

11. The disposable diaper according to claim 10, wherein the first and second regions of the absorber include an absorbent core.

12. The disposable diaper according to claim 1, wherein the absorber has a center in the product widthwise direction, and the crotch stretch unit extends across the center of the absorber.

13. The disposable diaper according to claim 1, wherein the crotch stretch unit is a stretchable sheet overlapping an absorbent core of the absorber in the product thickness direction.

14. The disposable diaper according to claim 3, wherein the plurality of compressed units overlaps the crotch stretch unit in the product thickness direction.

* * * * *